US007749738B2

(12) United States Patent
Jayaraman et al.

(10) Patent No.: US 7,749,738 B2
(45) Date of Patent: Jul. 6, 2010

(54) MICROBIAL PROCESS FOR ARGININE PRODUCTION

(75) Inventors: Gowrishankar Jayaraman, Hyderabad (IN); Madhusudan R. Nandineni, Hyderabad (IN)

(73) Assignee: Centre for DNA Fingerprinting and Diagnostics, Hyderabad (IN)

( * ) Notice: Subject to any disclaimer, the term of this patent is extended or adjusted under 35 U.S.C. 154(b) by 86 days.

(21) Appl. No.: 11/015,786

(22) Filed: Dec. 20, 2004

(65) Prior Publication Data

US 2005/0282258 A1    Dec. 22, 2005

(30) Foreign Application Priority Data

Mar. 10, 2004    (IN)    ............ 209/CHE/2004

(51) Int. Cl.
*C12P 13/10*    (2006.01)
*C12P 13/04*    (2006.01)
*C12N 1/20*    (2006.01)
*C12N 15/00*    (2006.01)
*C12N 15/74*    (2006.01)

(52) U.S. Cl. ............ 435/114; 435/106; 435/252.33; 435/252.3; 435/320.1; 435/471; 435/476

(58) Field of Classification Search ............ None
See application file for complete search history.

(56) References Cited

U.S. PATENT DOCUMENTS

| 4,430,430 | A | 2/1984 | Momose et al. | |
| 2003/0113899 | A1* | 6/2003 | Yamaguchi et al. | ...... 435/252.1 |

FOREIGN PATENT DOCUMENTS

| EP | 1 016 710 | 7/2000 |
| EP | 1 170 361 | 1/2002 |

OTHER PUBLICATIONS

Celis RT., Repression and activation of arginine transport genes in *Escherichia coli* K12 by the ArgP protein. JMB., 1999, vol. 294 (5): 1087-95.*
Whisstock et al., Prediction of protein function from protein sequence and structure. Q. Rev Biophys., 2003, vol. 36(3): 307-340.*
Tian et al., Explanation for different types of regulation of arginine biosynthesis in *Escherichia coli* B and *Escherichia coli* K12 caused by a difference between their arginine repressors. J. Mol. Biol., 1994, vol. 235: 221-230.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of a b-ketoacyl synthase to a malonyl decarboxylase by replacement of the active-site cysteine with glutamine. Biochemistry, 1999, vol. 38: 11643-11650.*
Kisselev L., Polypeptide release factors in prokaryotes and eukaryotes: same function, different structure. Structure, 2002, vol. 10: 8-9.*
Sousa et al., The ARO4 gene of *Candida albicans* encodes a tyrosine-sensitive DAHP synthase: evolution, functional conservation and phenotype of Aro3p-, Aro4p-deficient mutants. Microbiology, 2002, vol. 148: 1291-1303.*
Celis TRF., Repression and activation of arginine transport genes in *Escherichia coli* K 12 by the ArgP protein. J. Mol. Biol., 1999, vol. 294: 1087-1095.*
Mass WK., The Arginine repressor of *Escherichia coli*. Microbiol. Reviews., 1994, vol. 58 (4): 631-640.*
Rosen BP., Basic amino acid transport in *Escherichia coli*: Properties of canavanine-resistant mutants. J. Bacteriol., 1973, vol. 116 (2): 627-635.*
Andrews et al. (1991). "Mutational Analysis of Repression and Activation of the *tyrP* Gene in *Escherichia coli*," *Journal of Bacteriology* 173(16): 5068-5078.
Bellman et al. (2001). "Expression control and specificity of the basic amino acid exporter LysE of *Corynebacterium glutamicum*," *Microbiology* 147: 1765-1774.
Blattner et al. (1997). "The Complete Genome Sequence of *Escherichia coli* K-12," *Science* 277 (5331): 1453-1462.
Celis, Roberto T.F. (1999). "Repression and Activation of Arginine Transport Genes in *Escherichia coli* K 12 by the ArgP Protein," *Journal of Molecular Biology* 294(5): 1087-1095.
Covarrubias and Bolivar. (1982). "Construction and characterization of new cloning vehicles," *Gene* 17: 79-89.
Glansdorff, Nicolas. (1996). "Biosynthesis of Arginine and Polyamines," Chapter 25 In *Escherichia coli and Salmonella: Cellular and Molecular Biology*, 2nd Edition, Neidhardt, Frederick C. ed., ASM Press: Washington, D.C., pp. 408-433.
Kelln and O'Donovan. (1976). "Isolation and Partial Characterization of an *argR* Mutant of *Salmonella typhimurium*," *Journal of Bacteriology* 128(2): 528-535.
Kohara et al. (1987). "The Physical Map of the Whole *E. coli* Chromosome: Application of a New Strategy for Rapid Analysis and Sorting of a Large Genomic Library," *Cell* 50: 495-508.
Lerner and Inouye. (1990). "Low copy number plasmids for regulated low-level expression of cloned genes in *Escherichia coli* with blue/white insert screening capability," *Nucleic Acids Research* 18(15): 4631.
Miller, Jeffrey H. (1992). *A Short Course in Bacterial Genetics: A Laboratory Manual and Handbook for Escherichia coli and Related Bacteria*. Cold Spring Harbor Laboratory Press, Cold Spring Harbor Laboratory, New York, Table of Contents; 29 pages.

(Continued)

*Primary Examiner*—Ganapathirama Raghu
(74) *Attorney, Agent, or Firm*—Morrison & Foerster LLP

(57) ABSTRACT

The present invention relates to process for increased yield of the amino acid arginine from bacterial cultures by employing strains that have been genetically manipulated for both increased arginine biosynthesis and increased level of the *Escherichia coli* protein YggA or a protein that is substantially similar to *Escherichia coli* YggA. Two strains of this invention have been deposited at MTCC, Chandigarh. The strains are GJ4894/pHYD952 (MTCC 5127) and GJ4536/pHYD953 (MTCC 5128).

5 Claims, No Drawings

OTHER PUBLICATIONS

Rajagopal et al. (1998). "Use of Inducible Feedback-Resistant N-Acetylglutamate Synthetase (*argA*) Genes for Enhanced Arginine Biosynthesis by Genetically Engineered *Escherichia coli* K-12 Strains," *Applied and Environmental Microbiology* 64(5): 1805-1811.

Sambrook et al. (1989). *Molecular Cloning: A Laboratory Manual, Second Edition*, Cold Spring Harbor Laboratory Press, Cold Spring Harbor Laboratory, New York, Table of Contents; 90 pages.

Vrljic et al. (1996). "A new type of transporter with a new type of cellular function: L-lysine export from *Corynebacterium glutamicum*," *Molecular Microbiology* 22(5): 815-826.

Gorini et al. (Jul. 1961). "Induction by Arginine of Enzymes of Arginine Biosynthesis in *Escherichia coli* B," *Proceedings of the National Academy of Sciences of the United States of America* 47 (7-12): 961-971, 1701.

Kadner et al. (1971). "Regulatory Gene Mutations Affecting Arginine Biosynthesis in *Escherichia coli*," *Molecular & General Genetics* 111:1-14.

Jacoby et al. (1969). "A Unitary Account of the Repression Mechanism of Arginine Biosynthesis in *Escherichia coli*," *Journal of Molecular Biology* 39: 73-87.

Jacoby et al. (1967). "Genetics of Control of the Arginine Pathway in *Escherichia coli* B and K," *Journal of Molecular Biology* 24:41-50.

Maas. (1962). "Studies on Repression of Arginine Biosynthesis in *Escherichia coli*," *Cold Spring Harbor Symposia on Quantitative Biology* vol. XXVI: 183-191.

Makarova et al. (2001). "Conservation of the binding site for the arginine repressor in all bacterial lineages," *Genome Biology* 2(4): 0013.1-0013.9.

\* cited by examiner

MICROBIAL PROCESS FOR ARGININE PRODUCTION

FIELD OF INVENTION

The present invention relates to process for increased yield of the amino acid arginine from bacterial cultures by employing strains that have been genetically manipulated for increased arginine biosynthesis. Two strains of this invention have been deposited at MTCC, Chandigarh. The strains are GJ4894/pHYD952 (MTCC 5127) and GJ4536/pHYD953 (MTCC 5128).

PRIOR ART

Several amino acids, that are the constituents of naturally occurring proteins, are being produced commercially for use, for example, in the processed food industry, in animal stock feed, and in providing human parenteral nutrition supplements. Depending on the amino acid, the process for commercial production may be by chemical synthesis, protein hydrolysis, and/or microbial fermentation processes. Glutamate, for example, is produced in very large scale by bacterial fermentation.

Several features have been recognized as desirable in any process employing bacteria for amino acid production. One is to enhance or optimize the flux through the biosynthetic pathway of the amino acid. Another is to inactivate the active uptake systems for the amino acid in the bacterium so as to avoid its intracellular accumulation. Yet another, which has been recently recognized, is to exploit the function of amino acid exporters in bacteria.

Unlike the amino acid active uptake systems, very few amino acid exporters have been identified in the bacteria. Amongst the first bacterial amino acid exporters to be identified was the lysine exporter LysE of *Corynebacterium glutamicum* [Vrljic et al (1996)]. Subsequently, LysE was shown also to be an exporter of arginine [Bellmann et al (2001)]. LysE synthesis is under transcriptional activation control of the regulator protein LysG, which is a member of the large family of LysR-type transcriptional regulators. LysG mediates the induction both by lysine and by arginine of LysE transcription in *C. glutamicum*, as described in the reference of Bellmann et al (2001) cited above.

Arginine is classified as an essential amino acid in that it is required as a dietary constituent (most often as a component of dietary proteins) for most animals including humans. Regulation of arginine biosynthesis has been well studied in the bacteria of the family Enterobacteriaceae such as *Escherichia coli* or *Salmonella typhimurium*, where it has been shown that arginine biosynthesis is under repression control of the gene argR such that argR mutants exhibit substantially increased synthesis of the amino acid [N. Glansdorff (1996). The first enzyme of the arginine biosynthetic pathway, encoded by argA, is also subjected to feedback inhibition by the end-product arginine, and feedback inhibition-resistant argA mutants as well as *E. coli* derivatives with multicopy argA have been obtained that overproduce arginine [Momose et al, U.S. Pat. No. 4,430,430 1984; B. S. Rajagopal et al. (1998); L. R. Ptitsyn et al, EP1170361A2 2002]. Mutants that exhibit increased arginine synthesis are resistant to the arginine analog canavanine and are able to support increased syntrophic growth of arginine auxotrophic strains, as described in the references of Glansdorff (1996) and Kelln and O'Donovan (1976) cited above.

Several active uptake systems for arginine have been identified in *E. coli*; it has been claimed that arginine uptake through at least two of these uptake systems is controlled by the product of the argK gene whose transcription in turn is activated by a LysR-type transcriptional regulator gene argP (that was previously called iciA) [R. T. F. Celis (1999)]. It has further been claimed in the same reference of Celis (1999) that an argP mutation which confers resistance to canavanine does so by abolishing the activating function of ArgP on the arginine uptake systems.

V. A. Livshits et al (EP1016710 A2 2000) have suggested that the *E. coli* anonymous open reading frames yahN, yeaS, yfiK, and yggA encode amino acid exporters, and have shown that *E. coli* strains with multiple copies of yggA exhibit (i) enhanced resistance to arginine and to the lysine analog S-(2-aminoethyl)-cysteine, and (ii) enhanced production of lysine, glutamate, and arginine in the culture medium.

DEPOSIT OF STRAINS

In compliance with the requirements of full disclosure, two strains of this invention have been deposited on Feb. 19, 2004 in the Microbial Type Culture Collection (MTCC), Institute of Microbial Technology, Sector 39-A, Chandigarh 160036, India (according to international deposition based on Budapest Treaty). The strains are (accession numbers shown in parentheses):

GJ4894/pHYD952 (MTCC 5127)
GJ4536/pHYD953 (MTCC 5128)

OBJECTS OF THE INVENTION

The main object of the present invention is to provide a process for obtaining increased yield of amino acid arginine from bacterial cell cultures.

Another object of the present invention is to provide a process for obtaining increased yield of amino acid arginine from bacterial cell cultures by genetically manipulating the bacterial strains for increased arginine biosynthesis.

Another object of the present invention is to produce a recombinant bacterial strain having two genetic manipulations for increased arginine biosynthesis which comprises of introducing a mutation in the argR gene that is associated with the phenotypes of canavanine resistance and the ability to support increased syntrophic growth of an arginine auxotroph.

Another object of the present invention is to produce alteration or mutations in the argP gene which is associated with the phenotype of canavanine resistance.

Another object of the invention is to provide the altered or mutated argP gene in a plasmid.

Another object of the invention to provide genetically manipulated *E. coli* strains for increased arginine biosynthesis.

SUMMARY OF THE INVENTION

Accordingly, the present invention provides a novel process for production of arginine in bacterial cultures, the process comprising growth of a bacterial strain bearing at least two genetic manipulations, one comprising a canavanine-resistance-conferring alteration in the *Escherichia coli* argR gene and another comprising a canavanine-resistance-conferring alteration in the *Escherichia coli* argP gene. A critical feature of the invention is that the two genetic manipulations act synergistically, in that their combined effect on arginine production is substantially greater than that of either in isolation.

Another aspect of the invention is that the said second genetic manipulation is for an increased level of *E. coli* YggA that is achieved through increased transcription of the *E. coli* yggA gene, is defined as when undertaken in a second otherwise wild-type strain of the bacterium, the said second genetic manipulation will by itself be associated with a phenotype of canavanine resistance in the manipulated second bacterial strain.

Another aspect of the invention the said second genetic manipulation comprises introduction of a multicopy plasmid with the cloned *E. coli* yggA gene.

The invention also provides a method to genetically manipulate the bacterial strains for increased arginine biosynthesis in the bacterial cultures which comprises of the introduction of a mutation in the argR gene that is associated with the phenotypes of canavanine resistance and the ability to support increased syntrophic growth of an arginine auxotroph.

One more aspect of the present invention is to achieve increased level of said protein by introduction of a canavanine-resistance-conferring mutation in the argP gene, for example, an alteration of codon 94 of the *E. coli* argP gene Two strains of this invention have been deposited at MTCC, Chandigarh. The strains are GJ4894/pHYD952 (MTCC 5127) and GJ4536/pHYD953 (MTCC 5128)

BRIEF DESCRIPTION OF ACCOMPANYING SEQUENCE LISTINGS

5'-GGGCGCGAACTCGCTGAGCGA-3'      SEQ ID NO: 1

5'-GAGCAAGTTGTACGAACGCTT-3'      SEQ ID NO: 2

5'-GTAAAACGACGGCCAGT-3'          SEQ ID NO: 3

5'-AACAGCTATGACCATG-3'           SEQ ID NO: 4

DETAILED DESCRIPTION OF INVENTION

Accordingly, the present invention provides a process for production of arginine in bacterial cultures, said process comprising the steps of:

I. growing a first strain of a bacterium, the said first strain bearing at least two genetic manipulations comprising:

a first manipulation for increased arginine biosynthesis, comprising a canavanine-resistance-conferring alteration in the *Escherichia coli* argR gene the said first manipulation being defined as that which, when undertaken in a second otherwise wild-type strain of the said bacterium, is by itself associated with the phenotypes of canavanine resistance and the ability to support increased syntrophic growth of an arginine auxotroph, and (ii) a second manipulation comprising a canavanine-resistance-conferring alteration in the *Escherichia coli* argP gene, and II. then recovering, by known methods, arginine from the culture medium of the said first bacterial strain.

An embodiment of the invention provides a process, wherein the said bacterial strains is *Escherichia coli*.

The second genetic manipulation comprises a canavanine-resistance-conferring alteration in the argP gene and wherein the alteration in the argP gene comprises a leucine-encoding codon at codon position 94 of the *Escherichia coli* argP gene.

Another embodiment of the present invention, the alteration in argP is present on a plasmid, wherein the said plasmid is pHYD953 that is obtainable from the bacterium having the accession number MTCC 5128.

In another embodiment of the invention, the first genetic manipulation comprises a canavanine-resistance-conferring mutation in the argR gene.

The present invention relates to novel processes for production of arginine in bacterial cultures.

One aspect of the invention features a process for production of arginine in a bacterial culture, the process comprising growth of a first strain of a bacterium, the first strain bears genetic manipulation for increased arginine biosynthesis.

In one aspect of the invention, the increased level of the protein is achieved by introduction of a canavanine-resistance-conferring mutation in the argP gene, for example, an alteration of codon 94 of the *E. coli* argP gene to one encoding leucine.

In another aspect of the invention, the increased level of the protein is achieved by introduction of the yggA gene on a multicopy plasmid into the bacterium.

Preferably the bacterial strains are of bacteria of the family Enterobacteriaceae, for example, *E. coli*.—Wherein the said bacterium is *Escherichia coli*.

In a further- aspect of the invention, genetic manipulation for increased arginine biosynthesis in the first strain of the bacterium comprises introduction of a mutation in the argR gene that is associated with the phenotypes of canavanine resistance and the ability to support increased syntrophic growth of an arginine auxotroph.

As used herein "canavanine resistance" or "canavanine supersensitivity" associated with or conferred by a mutation or genetic manipulation is the ability of a strain carrying the said mutation or genetic manipulation to exhibit in culture media supplemented with various concentrations of canavanine, improved growth or reduced growth, respectively, over an isogenic wild-type strain not carrying the said mutation or genetic manipulation.

As used herein "the ability to support increased syntrophic growth of an arginine auxotroph" associated with or conferred by a mutation or genetic manipulation is the ability of a first test strain carrying the said mutation or genetic manipulation to exhibit, in comparison to a second isogenic wild-type test strain not carrying the said mutation or genetic manipulation, a more pronounced halo of syntrophic growth of microcolonies of an arginine auxotrophic indicator strain seeded into an arginine-free agar medium on the surface of which the test strains have been spotted, as illustrated for example in example 6.

Unless otherwise defined, all technical and scientific terms used herein have the same meaning as commonly understood by one of ordinary skill in the art to which this invention belongs. In case of conflict, the present application, including definitions, will control. All publications, patents, and other references mentioned herein are incorporated by reference.

Although methods and materials similar or equivalent to those described herein can be used in the practice or testing of the present invention, the preferred methods and materials are described below. The materials, methods, and examples are illustrative only and are not intended to be limiting. Other features and advantages of the invention will be apparent from the detailed description, and from the claims.

These methods are based on discoveries of certain novel properties of argP genes and mutations in them, as described herein. The discoveries include the findings that the loss of ArgP function in *E. coli* is associated, not with canavanine resistance as taught in the reference of Celis (1999) cited above but with canavanine-supersensitivity; that the loss of YggA function in *E. coli* is also associated with canavanine-supersensitivity; that in strains carrying the wild-type argP gene, transcription of the yggA gene is induced upon introduction of a canavanine resistance-conferring mutation in the argR gene or upon supplementation of the culture medium with arginine, its precursor citrulline, or canavanine, and that it is substantially repressed upon supplementation of the culture medium with lysine; and that in strains carrying canavanine resistance-conferring missense mutations in the argP gene, transcription of the yggA gene is elevated and is rendered largely constitutive of the effects of arginine or lysine supplementation to the cultures. These findings lead us to propose that the YggA protein is an exporter specific for arginine in *E. coli*, whose synthesis is under transcription activation control of the ArgP protein that mediates the inducing effect of arginine but is rendered inactive for its activation function in the presence of lysine.

The reference of Livshits et al (2000) cited above teaches a method for increased arginine production in a culture of a bacterial strain that has been genetically manipulated to exhibit an increased amount of *E. coli* YggA. However, the genetic manipulation is also associated with (i) increased lysine content in the culture medium, (ii) increased resistance to the lysine analog S-(2-aminoethyl)-cysteine which also implies increased lysine export, and (iii) increased glutamate content in the culture medium.

The method for increased arginine production taught by the reference of Livshits et al (2000) cited above is perceived in the art to suffer from several disadvantages, including but not limited to the following. Increased content of lysine and glutamate in the culture medium represent wasteful channeling of metabolites into products other than the desired end product arginine. Furthermore, the excreted glutamate itself is an essential precursor of arginine biosynthesis, and lysine will inhibit the synthesis of the YggA exporter (see example 6 below).

Accordingly, the present invention teaches improved methods for production of arginine in bacterial cultures that employ a first strain of a bacterium, one comprising a canavanine-resistance-conferring alteration in the *Escherichia coli* argR gene and another comprising a canavanine-resistance-conferring alteration in the *Escherichia coli* argP gene. A critical feature of the invention is that the two genetic manipulations act synergistically, in that their combined effect on arginine production is substantially greater than that of either in isolation.

A preferred aspect of the invention is that the second genetic manipulation is for an increased level of *E. coli* YggA that is achieved through increased transcription of the *E. coli* yggA gene. When undertaken in a second otherwise wild-type strain of the bacterium, the second genetic manipulation will by itself be associated with a phenotype of canavanine resistance in the manipulated second bacterial strain.

In one aspect of the invention, the second genetic manipulation comprises introduction of a multicopy plasmid with the cloned *E. coli* yggA gene, and Example 1 describes the construction of a multicopy plasmid pHYD952 with the cloned yggA gene.

In another aspect of the invention, the second genetic manipulation comprises introduction of a canavanine-resistance-conferring mutation in the argP gene, and Examples 2 to 4, taken together, describe a method for obtaining a plasmid pHYD953 with a canavanine-resistance-conferring mutation in the argP gene. That a canavanine-resistance-conferring mutation in the argP gene is associated with increased transcription of the yggA gene is described in Example 6.

Orthologs of *E. coli* yggA and argP exist in several bacteria, and it is therefore feasible for the skilled artisan to undertake the second genetic manipulation, as described above and in the examples, with the orthologous genes or with variants of the *E. coli* genes and their orthologs Arginine biosynthesis is tightly regulated in many bacteria, but the art teaches several means to genetically manipulate a bacterium so that the regulatory mechanisms are perturbed and the intracellular biosynthesis of arginine is increased [see, for example, the references of Glansdorff (1996), Kelln and O'Donovan (1976); Momose et al (1984); Rajagopal et al (1998); Ptitsyn et al (2002) cited above]. Such genetic manipulations known to the art include but are not limited to mutations inactivating the argR repressor gene, mutations in argA rendering the encoded enzyme acetylglutamate synthase feedback resistant to arginine, and increase in copy number of the argA gene. Any genetic manipulation that increases arginine biosynthesis in a bacterium will confer on the bacterium the phenotype of canavanine resistance and the ability to support increased syntrophic growth of an arginine auxotroph.

The present invention teaches a method for increasing arginine production in a culture of a bacterium, wherein the said bacterium is *Escherichia coli* said bacterium possessing at least one first genetic manipulation that increases arginine biosynthesis and at least one second genetic manipulation that increases the level of either *E. coli* YggA or a protein that is substantially similar in its amino acid sequence to *E. coli* YggA. Example 5 describes the increased production of arginine in *E. coli* strains, as determined by the ability of said strains to support increased syntrophic growth of an arginine auxotroph. The said *E. coli* strains possess a first genetic manipulation comprising an argR mutation leading to increased arginine biosynthesis in combination with a second genetic manipulation comprising a plasmid with canavanine-resistance-conferring mutation in the cloned argP gene.

Example 6 describes a method to construct a yggA-lac operon fusion for measurement of in vivo transcription activity of the yggA promoter, and its use to demonstrate that in a derivative of the wild-type strain MC4100, the yggA promoter transcription is induced by arginine and is rendered nearly inactive by exogenous lysine supplementation; and that in a strain with a canavanine-resistance-conferring mutation in argP, yggA promoter transcription is constitutively activated. These changes in yggA promoter transcription activity are expected to lead to appropriate changes in the level of YggA protein in the bacterium.

The examples given are merely illustrative of the uses, processes and products such as vectors and strains claimed in this invention, and the practice of the invention itself is not restricted to or by the examples described. It is to be expected that additional configurations of the same invention, and/or alternative means by which it is reduced to practice, may be achieved by modifications that involve materials and processes that are already known and well established in the art. It may also be noted in this context that orthologs of the argR, argP, and yggA genes have been identified in a variety of Gram-negative and Gram-positive bacteria.

In the following examples, the following materials and methods were used throughout:

1. Bacteriological media materials were purchased from Difco Laboratories (P.O. Box 331058, Detroit, Mich. 48232-7058, USA). Antibiotics and fine chemicals including amino acids and canavanine were purchased from Sigma-Aldrich Corporation (P.O. Box 14508, St. Louis, Mo. 63178, USA). All amino acids and canavanine were the "L-"optical isomers. Restriction endonucleases and enzymes used during DNA cloning, as also the 17-merM13/pUC sequencing primer (−20) and the 16-mer M13/pUC reverse sequencing primer (−24), were obtained from New England Biolabs (32 Tozer Rd, Beverly, Mass. 01915-5599, USA). Other synthetic oligonucleotide primers were obtained from Eurogentec s.a., Liege Science Park, Rue Bois Saint Jean 5, 4102 Seraing, Belgium.

Nutrient and glucose-minimal growth media were derived, respectively, from LB and glucose-minimal A media described in "A Short Course in Bacterial Genetics: A Laboratory Manual and Handbook for *Escherichia coli* and Related Bacteria" by J. H. Miller (1992), Cold Spring Harbor Laboratory Press, Cold Spring Harbor, N.Y., USA. When needed, supplementation of minimal growth medium with particular amino acids to satisfy an auxotrophic requirement was at a final concentration of 40 micrograms/ml each. Antibiotics were used (when needed) at the following final concentrations (micrograms/ml): ampicillin (Amp), 100; tetracycline (Tet), 15; chloramphenicol (Cm), 30; kanamycin (Kan), 50; trimethoprim (Tp), 60; and spectinomycin (Sp), 50. Superscripts R and S are used to denote the phenotypes of resistance and sensitivity respectively. Stock solutions of Amp, Kan, and Sp were prepared in water, that of Tp in dimethylformamide, and those of Tet and Cm in ethanol. Canavanine was prepared as a stock solution of 20 mg/ml in water and used at different concentrations as described below. 0.1 M citrate buffer (pH 5.5) and 0.1 M phosphate buffer (pH 7.0) were prepared as described in the reference of Miller (1992) cited above.

2. The genotypes of *Escherichia coli* strains used in the examples are listed in the Table 1 below.

TABLE 1

| Strain | Genotype |
|---|---|
| DH5alpha | delta (argF-lac)U169 deoR recA1 endA1 hsdR17 phoA supE44 thi-1 gyrA96 relA1 (phi80dlacZ deltaM15) |
| MC4100 | delta (argF-lac)U169 rpsL150 relA1 araD139 flbB5301 deoC1 ptsF25 |
| SK2226 | delta (gpt-proA)62 lacY1 or lacZ4 tsx-33 glnV44 galK2 trpE3 hisG4 xylA7 mtl-1 zif-290::Tn10 delta argH1 |
| GJ4536 | MC4100 argP202::lambda p(lac)Mu-Kan |
| GJ4748 | MC4100 argR64 zhb-914::Tn10dCm |
| GJ4822 | MC4100 yggA::Tn10Tet |
| GJ4894 | GJ4748 yggA::Tn10dTet |

Strain DH5alpha is available from Invitrogen Life Technologies, 1600 Faraday Avenue, Carlsbad, Calif. 92008, USA. Strains MC4100 and SK2226 are available from the *E. coli* Genetic Stock Center, 830 Kline Biology Tower, MCD Biology Department, 266 Whitney Avenue., P.O. Box 20813, Yale University, New Haven, Conn. 06520-8193, USA. Plasmid-bearing derivatives of the strains GJ4536 (with plasmid pHYD953) and GJ4894 (with plasmid pHYD952) are strains of this invention that have been deposited under the accession numbers MTCC 5128 and MTCC 5127 respectively at the Microbial type Culture Collection (MTCC) at the address cited above. The spontaneous plasmid-free derivative of each of the deposited strains may be obtained by screening for an Amp$^S$ colony following three successive cycles of 1:10000 subculturing each in 10 ml of LB medium. Strain GJ4748 may be obtained by phage P1 transduction into MC4100 with a P1 lysate prepared on GJ4894, by selection for Cm$^R$ transductants and screening for a colony that is able to grow on glucose-minimal A medium supplemented with uracil and canavanine at 40 and 65 micrograms/ml, respectively, and that can thus be shown to have inherited the argR64 mutation; the transductional linkage value between the zhb-914::Tn10dCm in this experiment is approximately 20%. Strain GJ4822 may be obtained by phage P1 transduction into MC4100 with a P1 lysate prepared on GJ4894, by selection for a Tet$^R$ transductant.

3. Bacteriophage P1 was obtained from Prof. A. J. Pittard, Dept. of Microbiology and Immunology, University of Melbourne, Parkville, Victoria 3052, Australia, and is also available from the NCCB/CBS (The Netherlands Culture Collection of Bacteria), P.O. Box 85167, 3508 AD Utrecht, The Netherlands. Bacteriophage lambda clones 471 and 472 of the ordered lambda phage library of the *E. coli* genome was obtained from Dr. K. Isono, Dept. of Biology, Faculty of Science, Kobe University, Japan, and is described in Y. Kohara et al.; it is also available from the NCCB/CBS (The Netherlands Culture Collection of Bacteria) at the same address as that indicated above.

4. 5. Plasmid pCL1920 was obtained from Dr. M. Inouye, Dept. of Biochemistry, UMDNJ-Robert Wood Johnson Medical School, Piscataway, 08854-5635, USA, and is described in C. G. Lerner and M. Inouye (1990); this plasmid is also available from the NCCB/CBS (The Netherlands Culture Collection of Bacteria) at the same address as that indicated above. Plasmid pBR329 is described in L. Covarrubias and F. Bolivar [Gene (1982) 17:79-89] and is also available from both the American Type Culture Collection (ATCC), P.O. 1549, Manassas, Va. 20108, USA, and the NCCB/CBS at its address indicated above. Plasmid pBluescript II-KS was obtained from Stratagene Inc., 11011 N. Torrey Pines Road, La Jolla, Calif. 92037, U.S.A. Plasmid pMU575 was obtained from Prof. A. J. Pittard, Department of Microbiology and Immunology, University of Melbourne, Parkville, Victoria 3052, Australia and is described in A. E. Andrews et al (1991).

5. Procedures for P1 transduction, and for most other routine microbial genetic techniques were as described in the reference of Miller (1992) cited above. Canavanine tolerance of strains was tested in glucose-minimal A medium supplemented with various concentrations of canavanine, and growth was scored after 24 hours at 37° C. In some cases, uracil at 40 micrograms/ml was added to the medium to enhance the toxicity imposed by a given canavanine concentration. The wild-type *E. coli* strain MC4100 was resistant to 20 micrograms/ml of canavanine, but it was sensitive to 65 micrograms/ml of canavanine in the presence of uracil at 40 micrograms/ml. Unless mentioned otherwise, the procedures for preparation of plasmid and lambda phage DNAs, the preparation and cloning of DNA fragments, plasmid transformations, and DNA sequence determinations, were by the standard techniques described J. Sambrook et al (1989), Cold Spring Harbor Laboratory Press, Cold Spring Harbor Laboratory, N.Y., USA. Strain DH5alpha was used as recipient in transformation experiments involving cloning of DNA fragments into plasmid vectors.

6. Data on the DNA sequence of the *E. coli* genome were obtained from F. R. Blattner et al (1997). The Accession numbers in the GenBank sequence database for the entire *E. coli* genome is NC_000913 and that for the genomic segment carrying both yggA and argP is AE000375. The argP gene is annotated as iciA in the sequence deposition of AE000375.

EXAMPLES

Example 1

Cloning of E. coli yggA Gene in pBR329

The multicopy yggA+ plasmid pHYD952 was constructed in three steps as follows. Starting from DNA of lambda phage clone 472 from the ordered lambda phage library of the E. coli genome described in the reference of Kohara et al (1987) cited above, a 3.8-kb EcoRI fragment carrying the yggA+ gene was eluted from an agarose gel piece following agarose gel electrophoresis. The 3.8-kb fragment was then cloned into the EcoRI site of plasmid vector pBluescript-IIKS to generate the $Amp^R$ plasmid pHYD944. In the second step, pHYD944 was digested with HindIII and PstI to release a 1.2-kb fragment with yggA+, which was eluted from an agarose gel piece following agarose gel electrophoresis and then cloned into the HindIII and PstI sites of plasmid vector pBluescript-IIKS to generate the $Amp^R$ plasmid pHYD951. In the third step, pHYD951 was digested with BamHI and HindIII to release the same 1.2-kb fragment carrying the yggA+ gene along with a small region of the multiple-cloning-site region of pBluescript-IIKS. The 1.2-kb BamHI-HindIII fragment was purified from an agarose gel piece following agarose gel electrophoresis and then cloned into the BamHI and HindIII sites of plasmid vector pBR329 to generate the $Amp^R$ $Cm^R$ plasmid pHYD952.

To confirm that the plasmid pHYD952 contains the yggA+ sequence, a yggA::Tn10dTet strain GJ4822 (wherein the functional chromosomal copy is disrupted by the insertion of the transposon Tn10dTet) was separately transformed either with plasmid vector pBR329 or with plasmid pHYD952, and one resultant $Amp^R$ colony from each transformation experiment was tested for its ability to grow on a glucose-minimal A plate supplemented with Amp and canavanine at 20 micrograms/ml. After incubation at 37° C. for 24 hours, it was observed that the transformant colony with pCL1920 had not grown whereas that with pHYD952 had grown well, indicating that the 1.2-kb DNA sequence carried by pHYD952 was able to complement the yggA::Tn10dTet mutation in GJ4822.

When growth of a MC4100 derivative transformed with plasmid pHYD952 was compared with that of a MC4100 derivative transformed with plasmid pBR329 on a glucose-minimal A agar plate supplemented with Amp, 40 micrograms/ml of uracil, and 65 micrograms/ml of canavanine, the former but not the latter exhibited growth on the said plate following an incubation at 37° C. for 24 hours.

Example 2

Cloning of E. coli argP Gene in pCL1920

The argP+ gene was cloned into plasmid vector pCL1920 in two steps as follows. Starting from DNA of lambda phage clone 471 from the ordered lambda phage library of the E. coli genome described in the reference of Kohara et al (1987) cited above, a 2.9-kb BamHI-KpnI fragment carrying the argP+ gene was eluted from an agarose gel piece following agarose gel electrophoresis. This fragment was then cloned into BamHI-KpnI digested plasmid vector pCL1920 to generate a recombinant plasmid, pHYD913. In the next step, pHYD913 was digested with SalI to release a 1.86-kb chromosomal fragment, which was expected to carry the argP gene along with its promoter sequence; the 1.86-kb SalI fragment was eluted from an agarose gel piece following agarose gel electrophoresis and cloned into the SalI site of plasmid vector pCL1920 to generate the recombinant plasmids pHYD914 and pHYD915. The orientation, with respect to the plasmid vector sequence, of the said 1.86-kb SalI chromosomal insert fragment in plasmid pHYD915 is such that the XbaI and PstI sites of the vector that flank the SalI cloning site are situated towards the promoter-proximal and promoter-distal ends, respectively, of the argP gene, and the reverse is the case for plasmid pHYD914.

The authenticity of the plasmids pHYD914 and pHYD915 was checked by testing the ability of each to complement an argP202::Kan strain GJ4536 (whose chromosomal argP gene has been rendered non-functional due to a transposon insertion) for growth on a glucose-minimal A plate containing canavanine. Plasmids pCL1920, pHYD914, and pHYD915 were separately introduced into GJ4536 by transformation as described in the reference of Sambrook et al (1989) cited above and selection for $Sp^R$ colonies. A single colony each of GJ4536/pCL1920, GJ4536/pHYD914 and GJ4536/pHYD915 was picked from the transformation plates, and streaked on a glucose-minimal A plate supplemented with Sp and canavanine at 20 micrograms/ml; the plate was incubated at 37° C. after 24 hours. The plasmids pHYD914 and pHYD915, but not the plasmid vector pCL1920, conferred on strain GJ4536 the ability to grow on the canavanine-supplemented medium, indicating that both plasmids pHYD914 and pHYD915 contain the wild type argP+ sequence.

Example 3

Obtaining Canavanine-Resistance-Conferring Mutations in argP

An N-methyl-N-nitro-N-nitrosoguanidine (MNNG) mutagenesis approach was taken to isolate plasmid borne canavanine-resistance-conferring argP alleles. The method followed for MNNG mutagenesis was as described in the reference of Miller (1992) cited above. An overnight culture of strain MC4100/pHYD915 grown in LB supplemented with Sp was diluted 50-fold in 10 ml of LB supplemented with Sp in a 150-ml Erlenmeyer flask and grown at 37° C. to a culture optical density (at 600 nm) of 0.6. Cells from five ml of the culture were recovered by bench-top centrifugation, washed twice with an equal volume of 0.1 M citrate buffer (pH 5.5), and resuspended in the same volume of 0.1 M citrate buffer (pH 5.5). MNNG was prepared fresh as a 1 mg/ml stock solution in 0.1 M citrate buffer (pH 5.5) and added to cells at a final concentration of 50 micrograms/ml. The mixture was incubated for 30 minutes at 37° C., followed by washing twice with 0.1 M phosphate buffer (pH 7.0). The cells were finally resuspended and grown overnight at 37° C. in 20 ml of LB supplemented with Sp in a 150-ml Erlenmeyer flask. The surviving fraction of the cells after MNNG treatment (and prior to amplification by overnight culture) was measured and determined to be about 10%.

Plasmid DNA was isolated from the overnight amplified culture of the population of mutagenized cells and used for transformation into the argP::Kan null strain GJ4536, with a selection for $Sp^R$ colonies on LB medium supplemented with Sp. The $Sp^R$ colonies thus obtained were then purified on glucose-minimal A medium supplemented with Sp, and then tested for growth on glucose-minimal A plates supplemented with Sp, 40 micrograms/ml of uracil and 65 micrograms/ml of canavanine; growth on these plates was scored after incubation at 37° C. for 24 hours.

From approximately 800 colonies screened, seven mutants were obtained that were able to grow on the uracil- and canavanine-supplemented plates. In order to confirm that the canavanine-resistance phenotype was plasmid-borne, plasmid DNA was isolated from each of the seven canavanine-resistance mutants and transformed again into GJ4536 by selecting for Sp$^R$ colonies on LB medium supplemented with Sp. Eight to ten Sp$^R$ colonies from each transformation were purified on glucose-minimal A plates supplemented with Sp and then tested as described above for growth on glucose-minimal A plates supplemented with Sp, 40 micrograms/ml uracil and 65 micrograms/ml of canavanine, and incubation at 37° C. for 24 hours. The results showed that all the colonies in each case grew better than the control GJ4536/pHYD915, indicating that the plasmids confer a canavanine-resistance phenotype. The seven plasmids carrying canavanine-resistance-conferring mutations were designated from pHYD926 through pHYD932.

To determine whether the canavanine-resistance-conferring mutations obtained in the above experiment were recessive or dominant to the wild type argP allele, plasmids pHYD926 through pHYD932 were separately introduced into MC4100 (that is chromosomally argP$^+$) by transformation with selection for Sp$^R$ on LB medium supplemented with Sp at 37° C. The resultant Sp$^R$ colonies were tested along with the MC4100/pHYD915 as the control strain, for the canavanine-resistance phenotype as described above, by streaking on glucose-minimal A plates supplemented with Sp, 40 micrograms/ml of uracil and 65 micrograms/ml of canavanine, and incubation at 37° C. for 24 hours. MC4100 derivatives carrying six of the seven plasmids, namely pHYD926 through pHYD930 and pHYD932, were able to grow on the uracil- and canavanine-supplemented medium whereas MC4100/pHYD931 and MC4100/pHYD915 were unable to grow on the medium. Based on these results, it was concluded that the canavanine-resistance-conferring mutation in each of the plasmids pHYD926 through pHYD930 and pHYD932 is dominant to argP$^+$ whereas that in pHYD931 is recessive to argP$^+$.

To molecularly characterize the canavanine-resistance-conferring mutation in each of the plasmids, sequencing of the argP gene on the plasmids was undertaken by standard methods with the aid of (i) two primers internal to the 1.86-kb SalI fragment of the argP gene having SEQ ID NO:1 and SEQ ID NO: 2 [ARGP1, SEQ ID NO: 1 (5'-GGGCGC-GAACTCGCTGAGCGA-3') and ARGP2 SEQ ID NO: 2 (5'-GAGCAAGTTGTACGAACGCTT-3')] and (ii) the M13 pUC sequencing primer (−20) having SEQ ID NO: 3 [5'-GTAAAACGACGGCCAGT-3'] and M13/pUC reverse sequencing primer (−24) having SEQ ID NO: 4 [5'-AA-CAGCTATGACCATG-3'] that are able to read from the multiple-cloning-site region in the vector pCL1920. The sequencing results indicated that each of the seven plasmids harbored a GC-to-AT missense mutation at a different site in argP which was deduced to result in a single amino acid residue alteration in the encoded protein, as described in Table 2.

TABLE 2

| Plasmid | Mutated codon number in argP | Codon sequence alteration | Amino acid alteration |
|---|---|---|---|
| pHYD926 | 94 | TCA-to-TTA | Serine-to-Leucine |
| pHYD927 | 108 | CCT-to-TCT | Proline-to-Serine |
| pHYD928 | 144 | GTG-to-ATG | Valine-to-Methionine |
| pHYD929 | 217 | CCC-to-CTC | Proline-to-Leucine |
| pHYD930 | 294 | CTT-to-TTT | Leucine-to-Phenylalanine |
| pHYD931 | 295 | CGT-to-TGT | Arginine-to-Cysteine |
| pHYD932 | 68 | GCA-to-GTA | Alanine-to-Valine |

Example 4

Cloning of Canavanine-Resistance-Conferring argP Mutant Allele from pHYD926 into Plasmid Vector pBR329

The argP mutant allele from plasmid pHYD926 was subcloned into the multicopy plasmid vector pBR329 as follows. Plasmid pHYD926 was digested with SalI to release a 1.8-kb fragment, which was purified from an agarose gel piece following agarose gel electrophoresis. This fragment was cloned into the SalI site of pBR329 to generate plasmid pHYD953, transformants of which were selected as Amp$^R$ colonies. The orientation of the 1.8-kb argP-bearing SalI fragment in plasmid pHYD953 is such that the direction of argP transcription on the plasmid is opposite to that of transcription from the pBR329 vector-derived tet promoter on the plasmid.

When growth of a MC4100 transformed with plasmid pHYD953 was compared with that of a MC4100 derivative transformed with plasmid pBR329 on a glucose-minimal A agar plate supplemented with Amp, 40 micrograms/ml of uracil, and 65 micrograms/ml of canavanine, the former but not the latter exhibited growth on the plate following an incubation at 37° C. for 24 hours.

Example 5

Demonstration of Increased Arginine Production in argR Strains with Multicopy yggA$^+$ or with a Canavanine-Resistance-Conferring Mutation in argP That argR strains (derepressed for arginine biosynthesis) either with multicopy yggA$^+$ or with the argP-S94L allele exhibit substantially increased arginine production was demonstrated in an experiment wherein the ability of these strains to support syntrophic growth of an arginine auxotroph was tested. A pBR329 transformant derivative of the delta argH strain SK2226 was used as the arginine-auxotrophic indicator strain in the experiment. An overnight culture of the strain SK2226/pBR329 grown in LB supplemented with Amp was diluted in LB and 200 microliters of the 1:1000 dilution (corresponding to approximately 10$^5$ cells) was added to 40 ml of glucose minimal A-agar medium supplemented with proline, tryptophan, histidine (that is, with all auxotrophic requirements of SK2226 other than arginine), 1 microgram/ml of tetrazolium chloride, and Amp, when the temperature of the medium was around 40° C.; the agar medium was then poured into two 85 mm sterile petri dishes (20 ml per dish) and allowed to solidify at room temperature. Each of the agar plates was demarcated into three equal sectors and in the centre of each sector a test colony was spotted as specified below.

Strains MC4100 (which is argR$^+$) and GJ4748 (which is argR) were transformed separately with each of the plasmids pBR329, pHYD952, or pHYD953 with selection in all cases for Amp$^R$ colonies. The transformant colony derivatives of GJ4748/pBR329, GJ4748/pHYD952, and GJ4748/pHYD953 were spotted with sterile toothpicks as test colonies in the three sectors on the surface of one of the agar plates prepared as above, and the colonies of MC4100/pBR329, MC4100/pHYD952, and MC4100/pHYD953 were similarly spotted as the test colonies in the three sectors on the surface of the second agar plate; the plates were incubated at 37° C. After 12 hours of incubation, there was a prominent red halo caused by the syntrophic growth of SK2226/pBR329 microcolonies only around the spots of GJ4748/pHYD952 and GJ4748/pHYD953, indicative of substantially increased arginine production by these two strains in comparison with the other four strains. After 40 hours of incubation, GJ4748/pBR329 also exhibited a red halo of syntrophic growth of SK2226/pBR329 whereas the other three strain derivatives did not exhibit any such halo of growth of the indicator strain.

Example 6

Increased yggA Transcription in Strain with Canavanine-Resistance-Conferring argP Mutation For monitoring of yggA transcription in vivo, a single-copy-number plasmid pHYD956 with a yggA-lac operon fusion was constructed in two steps as follows. In the first step, plasmid pHYD951 (described in example 1) was digested with HindIII and PvuII to release a 1.1-kb fragment carrying the yggA transcriptional regulatory region and all but the 3'-end region of the yggA structural gene, and this fragment was eluted from an agarose gel piece following agarose gel electrophoresis. The fragment was cloned into the plasmid vector pBluescript-IIKS that had been digested with PstI and EcoRV, to generate the $Amp^R$ plasmid pHYD954. In the second step, plasmid pHYD954 was digested with PstI and HindIII to release the same 1.1-kb fragment along with a small region of the multiple-cloning-site region of pBluescript-IIKS. The 1.1-kb PstI-HindIII fragment was purified from an agarose gel piece following agarose gel electrophoresis and cloned into the plasmid vector pMU575 that had been digested with PstI and HindIII, to generate the $Tp^R$ plasmid pHYD956. Plasmid pMU575 has been described in Andrews et al (1991) and is a single-copy-number plasmid vector encoding $Tp^R$ which carries a promoter-less lacZ gene upstream of which promoter fragments can be cloned to generate promoter-lac operon fusions. Plasmid pHYD956 accordingly carries the yggA transcription-regulatory region cloned upstream of the lacZ gene of the pMU575 vector.

Plasmid pHYD956 was introduced by transformation into strains MC4100 and GJ4748 with selection for $Tp^R$ colonies, and into strain MC4100/pHYD926 with selection for $Sp^R Tp^R$ colonies. One pHYD956 transformant each of the three strains was then grown at 37° C. in glucose-minimal A media with the appropriate antibiotics and additionally without, or with, supplementation with 1 mM arginine or 1 mM lysine, for determination of betagalactosidase specific activities as described in the reference of Miller (1992) cited above. The results are tabulated in Table 3.

TABLE 3

| | Beta-galactosidase specific activity (units) in medium with | | |
|---|---|---|---|
| | Nil | 1 mM arginine | 1 mM lysine |
| MC4100/pHYD956 | 20 | 66 | 14 |
| GJ4748/pHYD956 | 217 | 424 | 29 |
| MC4100/pHYD926/pHYD956 | 1557 | 1514 | 1616 |

The results indicated that yggA transcription is induced by arginine in strain MC4100 and by the argR mutation of GJ4748, and that it is very low in both MC4100 and GJ4748 in the presence of lysine. Furthermore, the canavanine-resistance-conferring mutation in argP present in the MC4100/pHYD926 derivative was associated with high and constitutive yggA transcription.

REFERENCES CITED

Patents

Momose et al, U.S. Pat. No. 4,430,430, issued 7 Feb. 1984
L. R. Ptitsyn et al, European patent application EP1170361 A2, published 9 Jan. 2002
V. A. Livshits et al, European patent application EP1016710 A2, published 5 Jul. 2000

Publications

Vrljic et al (1996) Mol. Microbiol. 22: 815-826
Bellmann et al (2001) Microbiology 147: 1765-1774
N. Glansdorff (1996) "Biosynthesis of arginine and polyamines", in *Escherichia coli* and *Salmonella*: Cellular and Molecular Biology, $2^{nd}$ edition" (Neidhardt et al., eds), ASM Press, Washington D.C., USA, Chapter 25, pp. 408-433
R. A. Kelln and G. A. O'Donovan (1976) J. Bacteriol. 128: 528-535
B. S. Rajagopal et al. (1998) Appl. Env. Microbiol. 64: 1805-1811
R. T. F. Celis (1999) J. Mol. Biol. 294: 1087-1095
J. H. Miller (1992) "A Short Course in Bacterial Genetics: A Laboratory Manual and Handbook for *Escherichia coli* and Related Bacteria", CSH Press, Cold Spring Harbor Laboratory, New York, USA
Y. Kohara et al. (1987) Cell 50:495-508
C. G. Lerner and M. Inouye (1990) Nucleic Acids Res. 18:4631
L. Covarrubias and F. Bolivar (1982) Gene 17:79-89
A. E. Andrews et al (1991) J. Bacteriol. 173: 5068-5078
J. Sambrook et al. (1989) "Molecular Cloning: A Laboratory Manual, $2^{nd}$ Edition", CSH Press, Cold Spring Harbor Laboratory, New York, USA
F. R. Blattner et al. (1997) Science 277:1453-1462

We claim:

1. A process for production of arginine in bacterial cultures, said process comprising:
    a) growing a strain of an *Escherichia coli* bacterium, said strain bearing at least two genetic manipulations comprising:
        (i) a first manipulation for increased arginine biosynthesis, comprising a canavanine-resistance-conferring alteration in an endogenous *Escherichia coli* argR gene, the said first manipulation being defined as that which by itself is associated with the phenotypes of canavanine resistance and the ability to support increased syntrophic growth of an arginine auxotroph, and
        (ii) a second manipulation comprising a canavanine-resistance-conferring alteration in an *Escherichia coli* argP (ici A) gene, wherein the alteration in the argP gene comprises a mutation at a codon position selected from codon positions 94, 108, 144, 217, 294, 295 and 68 of the *Escherichia coli* argP gene, and
    b) recovering arginine from the culture medium of said bacterial strain.

2. The process of claim 1, wherein the alteration in the argP gene comprises a leucine-encoding codon at codon position 94 of the *Escherichia coli* argP gene.

3. The process as claimed in claim 1, wherein the argP gene with the alteration is present on a plasmid.

4. The process of claim 3, wherein the plasmid is pHYD953 that is obtainable from the bacterium having the accession number MTCC 5128.

5. A process for production of arginine in bacterial cultures, said process comprising:
    providing a strain of a bacterium from the family of Enterobacteriaceae that is capable of arginine production,
    genetically manipulating said strain of the bacterium to obtain a modified strain, said manipulation comprising:
        (i) a first mutation or alteration at an endogenous gene encoding for arginine repressor protein that is defined as that which by itself is associated with the phenotypes of canavanine resistance and the ability to support increased syntrophic growth of an arginine auxotroph;
        (ii) a second manipulation or alteration at an argP (ici A) gene that confers a canavanine-resistance, wherein the alteration in the argP gene comprises a mutation at a codon position selected from codon positions 94, 108, 144, 217, 294, 295 and 68 of the *Escherichia coli* argP gene and said argP gene alteration is present on a plasmid; and
        (iii) culturing the modified strain of bacteria, and harvesting arginine from the bacterial culture.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial sequence

```
<220> FEATURE:
<223> OTHER INFORMATION: Primer was synthesised for use.

<400> SEQUENCE: 1
gggcgcgaac tcgctgagcg a                                        21

<210> SEQ ID NO 2
<211> LENGTH: 21
<212> TYPE: DNA
<213> ORGANISM: Artificial sequence
<220> FEATURE:
<223> OTHER INFORMATION: Primer was synthesised for use.

<400> SEQUENCE: 2
gagcaagttg tacgaacgct t                                        21

<210> SEQ ID NO 3
<211> LENGTH: 17
<212> TYPE: DNA
<213> ORGANISM: Artificial sequence
<220> FEATURE:
<223> OTHER INFORMATION: Primer was synthesised for use

<400> SEQUENCE: 3
gtaaaacgac ggccagt                                             17

<210> SEQ ID NO 4
<211> LENGTH: 16
<212> TYPE: DNA
<213> ORGANISM: Artificial sequence
<220> FEATURE:
<223> OTHER INFORMATION: primer synthesised in lab.

<400> SEQUENCE: 4
aacagctatg accatg                                              16
```